(12) United States Patent
Kingsland et al.

(10) Patent No.: US 7,816,495 B2
(45) Date of Patent: Oct. 19, 2010

(54) PROCESSES FOR THE PREPARATION OF FIBRINOGEN

(75) Inventors: Sarah Kingsland, Stevenage (GB); Robert Clemmitt, Rotherhthe (GB); David Evans, Bushey (GB); Peter Feldman, Stanmore (GB)

(73) Assignee: NHS Blood and Transplant, Watford, Hertfordshire (GB)

( * ) Notice: Subject to any disclaimer, the term of this patent is extended or adjusted under 35 U.S.C. 154(b) by 693 days.

(21) Appl. No.: 10/520,436

(22) PCT Filed: Jul. 7, 2003

(86) PCT No.: PCT/GB03/02928

§ 371 (c)(1),
(2), (4) Date: Aug. 17, 2006

(87) PCT Pub. No.: WO2004/007533

PCT Pub. Date: Jan. 22, 2004

(65) Prior Publication Data

US 2007/0042944 A1 Feb. 22, 2007

(30) Foreign Application Priority Data

Jul. 10, 2002 (GB) .................. 0216001.8

(51) Int. Cl.
*A61K 35/36* (2006.01)
*C07K 14/75* (2006.01)
*C07K 14/745* (2006.01)

(52) U.S. Cl. ............... 530/382; 530/412; 530/413; 530/415; 530/416; 530/417

(58) Field of Classification Search .............. None
See application file for complete search history.

(56) References Cited

U.S. PATENT DOCUMENTS 5,169,936 A * 12/1992 Staples et al. ............... 530/350

| 5,445,958 A | 8/1995 | Feldman |
| 5,716,645 A | 2/1998 | Tse et al. |
| 6,268,487 B1 | 7/2001 | Kutzko et al. |

FOREIGN PATENT DOCUMENTS

| JP | 02-000114 | | 1/1990 |
| JP | 02 193913 | A | 7/1990 |
| JP | 06-138127 | | 5/1994 |
| JP | 08 012586 | A | 1/1996 |
| JP | 08 333387 | A | 12/1996 |
| JP | 2001-270900 | | 10/2001 |
| WO | WO 90/12803 | | 11/1990 |
| WO | WO 94/02183 | A1 | 2/1994 |
| WO | WO 95/23167 | A1 | 8/1995 |
| WO | WO 95/25748 | A1 | 9/1995 |
| WO | WO 96/17631 | A1 | 6/1996 |
| WO | WO 9617631 | * | 6/1996 |
| WO | WO 99/20749 | A1 | 4/1999 |
| WO | WO 99/23111 | A1 | 5/1999 |
| WO | WO 00/09540 | A1 | 2/2000 |

OTHER PUBLICATIONS

Chaga et al, J Biochem Biophys Methods 49: 313-334, 2001.*
United Kingdom Search Report dated May 16, 2003 from priority application serial No. GB 0216001.8.
United Kingdom Search Report dated Dec. 18, 2002 from priority application serial No. GB 0216001.8.
Millpore Product Catalogue—Product category prosep chromatography media, 'Online! 1999, pp. 1-2, XP002256821.
Parameswaran, R. et al. (2000) "Spontaneous intracranial bleeding in two patients with congenital afibrinogenaemia and the role of replacement therapy" Haemophilia 6:705-708.
Hari, P.R. et al. (2000) "Adsorption of human IgC on Cu2+ -immobilized cellulose affinity membrane: preliminary study" Journal of Biomedical Material Research 50:110-113.

* cited by examiner

*Primary Examiner*—Phuong Huynh
(74) *Attorney, Agent, or Firm*—Knobbe Martens Olson & Bear LLP

(57) ABSTRACT

The present invention relates to processes for the purification of fibrinogen, and to readily solubilised fibrinogen preparations.

14 Claims, No Drawings

PROCESSES FOR THE PREPARATION OF FIBRINOGEN

RELATED APPLICATIONS

This application is a U.S. National Phase under 35 U.S.C. 371 of International Application No.: PCT/GB2003/002928, filed Jul. 7, 2003 designating the U.S. and published in English on Jan. 22, 2004 as WO 2004/007533, which claims the benefit of British patent application No. GB 0216001.8, filed Jul. 10, 2002.

FIELD OF INVENTION

The present invention relates to processes for the purification of fibrinogen, and to readily solubilised fibrinogen preparations.

BACKGROUND OF THE INVENTION

Fibrinogen is a blood plasma protein which is concerned in clot formation. It is converted into fibrin monomer by the action of the plasma protease thrombin. Fibrin monomers cluster together to form a weak clot and are then cross-linked by the action of activated factor XIII (i.e. factor XIIIa) to a form a stronger clot. Fibrinogen is used in therapy in combination with thrombin in the so-called fibrin sealants to achieve haemostasis, to seal wounds and for the controlled adhesion of tissue. Fibrinogen concentrates are also used for replacement therapy treatment of patients with fibrinogen deficiency (afibrinogenaemia) which may be inherited or acquired.

For all clinical applications, it is important to have highly pure fibrinogen in order to minimise any undesirable side effects resulting from, for example, the presence of unwanted contaminating proteins. In particular, it is desirable for fibrinogen preparations for clinical use to be free of plasminogen and plasmin (Blomback B., Blomback M., "Purification of human and bovine fibrinogen", Arkiv for Kemi 1956; 10:415-443, and Mosesson M. W., "The preparation of human fibrinogen free of plasminogen", Biochim Biophys Acta 1962, 57:204-213). Plasminogen is the inactive precursor of plasmin, a fibrinolytic enzyme which digests fibrin clots. Therefore the presence of plasminogen in a fibrinogen preparation intended for use in vivo is undesirable because any plasmin generated from the plasminogen at the site of clot formation may then destabilise the clot.

Plasminogen tends to co-purify with fibrinogen and its removal can be difficult. Some clinical fibrinogen preparations therefore contain anti-fibrinolytic agents to inhibit any plasmin or plasminogen present (e.g. aprotinin, a bovine protein inhibitor of plasmin; or tranexamic acid, a synthetic plasmin inhibitor also associated with neurotoxic side-effects). One advantage of separating plasminogen from fibrinogen is that there is then no need to use such fibrinolytic inhibitors in the clinical fibrinogen preparation.

In addition, it is highly desirable that fibrinogen derived from human or animal sources is treated to inactivate any blood-borne viruses which may be present, for example hepatitis virus or HIV. Various methods of virus inactivation are known in the art, including pasteurisation, dry heat treatment and solvent-detergent treatment (Pathogen Inactivation of Labile Blood Products, Council of Europe Expert Committee and Blood Transfusion Study Group on Pathogen Inactivation in Labile Blood Products, *Transfusion Medicine*, 2001, 11, 149-175).

Dry heat treatment is known to be effective for the inactivation of both enveloped and some non-enveloped viruses, whilst solvent-detergent treatment is known to be effective for the inactivation of enveloped (i.e. lipid coated) viruses such a hepatitis B.

Various methods for the purification of fibrinogen are known in the art. However, prior art purification methods suffer from various disadvantages. For example, precipitation methods do not allow easy incorporation of a solvent-detergent (SD) virus inactivation step, as the removal of SD reagents is much more efficiently effected chromatographically. Chromatography methods may not separate fibrinogen from plasminogen in a single step, which may lead to the need for additional chromatography to adsorb plasminogen, or the need to add an anti-fibrinolytic agent to the final fibrinogen preparation to combat residual plasminogen. In addition, not all the prior art methods are suitable for the purification of fibrinogen from a wide range of fibrinogen-containing solutions (including plasma and recombinant fractions).

U.S. Pat. No. 5,169,936 has previously suggested that immobilised metal ion affinity chromatography (IMAC) might be used in the preparation of human fibrinogen. However, no examples of such a method are disclosed, nor is there any suggestion that IMAC might be used for the separation of fibrinogen from plasminogen.

It is also known that the dissolution of fibrinogen concentrates can be difficult, and often requires the use of elevated temperatures or prolonged stirring (see U.S. Pat. No. 5,260,420 and EP-A 0804933). Due to the instability of liquid solutions of fibrinogen over time, fibrinogen preparations for clinical use are marketed either in the form of a deep-frozen solution or as a lyophilisate (i.e. a freeze dried preparation). Before use, the commercial product must be either thawed or reconstituted from the lyophilisate. Both these measures require significant time and effort.

It would therefore be advantageous to provide alternative methods for the purification of fibrinogen, in particular a method which is applicable to any fibrinogen containing starting material and which allows incorporation of one or more virus inactivation steps. It would also be advantageous to provide a method for the separation of fibrinogen from plasminogen. Furthermore, it would be advantageous to provide a lyophilised, and preferably heat treated, fibrinogen concentrate which can be readily redissolved at room temperature.

SUMMARY OF THE INVENTION

In one aspect, the present invention therefore provides a method for the separation and purification of fibrinogen and at least one other protein which comprises the steps of:

(a) loading a solution comprising fibrinogen and at least one other protein onto an immobilised metal ion affinity chromatography matrix under conditions such that the fibrinogen and the at least one other protein both bind to the matrix, and (b) selectively eluting the fibrinogen and the at least one other protein separately from the matrix. The fibrinogen and the at least one other protein may be collected separately and each processed further as required.

Preferably, the solution comprising fibrinogen is a fibrinogen-containing plasma fraction. Preferably, the at least one other protein is plasminogen.

In a further aspect, the present invention provides a method for the separation of fibrinogen from plasminogen comprising use of immobilised metal ion affinity chromatography. Preferably, the method comprises the steps of:

(a) loading a solution comprising fibrinogen and plasminogen onto an immobilised metal ion affinity chromatography matrix under conditions such that at least the fibrinogen binds to the matrix, and (b) selectively eluting the fibrinogen from the matrix. Preferably the plasminogen also binds to the matrix, and the plasminogen and the fibrinogen may be selectively eluted separately from the matrix.

DETAILED DESCRIPTION OF THE PREFERRED EMBODIMENT

As used herein, references to the separation and/or purification of fibrinogen include the joint separation and/or co-purification of fibrinogen and factor XIII together from starting materials comprising both fibrinogen and factor XIII.

The starting material for the methods of the invention may be any fibrinogen-containing solution, including human or animal plasma or a plasma fraction, cell culture fractions from recombinant technology, fractions derived from milk from transgenic animals, etc. Preferred starting materials are plasma fractions such as cryoprecipitate, heparin precipitate and cold precipitate. More preferred starting materials include heparin precipitate and cryoprecipitate. Other preferred starting materials include those further comprising plasminogen and/or factor XIII.

The starting material may be prepared by any suitable method known in the art, including via gene manipulation, for example in cell culture or transgenic species. For example, cryoprecipitate may be prepared according to the method of Gunson H. H., Bidwell E., Lane R. S., Wensley R. T., Snape T. J., "Variables involved in cryoprecipitate production and their effect on Factor VIII activity", British Journal of Haematology, 1978; 43:287-295; heparin precipitate may be prepared according to the method of Winkelman L., Owen N. E., Evans D. R., Evans H. E., Haddon M. E., Smith J. K., Prince P. J., Williams J. D., Lane R. S., "Severely heated therapeutic Factor VIII concentrate of high specific activity", Vox Sanguinis, 1989; 57:97-103; and cold precipitate according to the method of Smith J. K., Evans D. R., Stone V., Snape T. J., "A Factor VIII concentrate of intermediate purity and higher potency", Transfusion, 1979; 19:299-306.

Unwanted contaminants in the starting material which may be separated from the fibrinogen using the methods of the invention may include other proteins (for example plasma proteins such as plasminogen), reagents from earlier processing steps (for example elements of cell culture media or solvent-detergent reagents), viruses and prions. It is particularly preferred that plasminogen be removed, so that the addition of plasmin inhibitors (anti-fibrinolytic agents) to the fibrinogen may be avoided.

The fibrinogen-containing solution is loaded onto an IMAC matrix. Preferably, the matrix is present in a column for ease of processing. Any suitable metal ion may be used, for example copper, zinc or nickel, preferably copper. Suitable immobilised metal ion affinity chromatography gels for use in the process of the invention include methacrylate gel with multi-substituted ligands on the side chain spacers (e.g. Fractogel EMD Chelate from Merck), methacrylate gel with single chelating groups on the spacer arm (e.g. Toyopearl Chelate from Tosoh Biosep) and cross-linked agarose gel (e.g., chelating Sepharose FF from Amersham Biosciences). A preferred gel is Toyopearl AF chelate 650(M) from Tosoh Biosep.

The loading conditions, including the buffer used, should be chosen such that the fibrinogen, and any factor XIII if present, in the starting material are bound to the gel. Unwanted contaminants which do not bind to the gel may then be removed by washing. For example, if the starting material has previously been subjected to a solvent-detergent inactivation step, any solvent or detergent reagents remaining do not bind to the gel and are easily removed by washing. Alternatively, if the unwanted contaminants bind to the gel they may be removed by selective elution before the fibrinogen is eluted, or they may remain bound to the gel whilst the fibrinogen is selectively eluted. Additionally, washing the gel and bound protein(s) may also help to remove any viruses which may be present in the chromatography feedstocks.

It has been found that plasminogen binds less tightly than fibrinogen or factor XIII to metal chelate chromatography gels. Any plasminogen present in the starting material may therefore be removed by washing, by selective elution using a low concentration solution of low molecular weight competitive chelating compound, or by changing conditions so as to reduce the binding strength, for instance by reducing the pH or ionic strength, whilst the fibrinogen remains bound. Suitable chelating compounds include amino acids, for example alanine, leucine and lysine, imidazole, citrate salts and ethylenediaminetetraacetic acid (EDTA). A preferred chelating compound for the elution of plasminogen is alanine. The concentration of the chelating compound should be chosen such that plasminogen is eluted whilst the fibrinogen remains bound to the gel. The exact concentration will depend on the eluant used. For example, concentrations of <about 20 mM should selectively remove plasminogen in the presence of bound fibrinogen. Suitable concentrations for the elution of plasminogen include $\leq$20 mM of alanine or leucine, $\leq$10 mM lysine and <10 mM imidazole.

The fibrinogen may then be eluted using a higher concentration of the same or a different chelating compound, or by reducing the pH or ionic strength. Preferred chelating compounds for the elution of fibrinogen are amino acids, preferably lysine or arginine, and imidazole. A more preferred eluant comprises arginine. For example, the fibrinogen may be eluted using a >20 mM solution of the chelating compound. The conditions for the elution of the fibrinogen (concentration and pH) should be chosen such that the fibrinogen is removed from the gel but the metal ion is not, in order to minimise contamination of the product with metal ions.

Removal of plasminogen is advantageous as the fibrinogen may then be used clinically without the need for addition of any anti-fibrinolytic to the clinical preparation. A further advantageous feature is that the plasminogen which has been separated from the fibrinogen by IMAC may then be further processed to yield a plasminogen concentrate for clinical use. IMAC may therefore be used to prepare both plasminogen and fibrinogen from a starting solution comprising both plasminogen and fibrinogen.

It is an advantageous feature of the processes of the invention that any factor XIII in the starting material tends to co-elute with the fibrinogen. The presence of measurable (>1 u/ml) factor XIII in the final fibrinogen preparations may be beneficial if the fibrinogen is to be used clinically. It has been shown that the concentration of factor XIII has an effect in some in vitro tests of fibrin sealants, although there is no evidence that factor XIII is required for clinical efficacy, and fibrin sealant products with no measurable factor XIII activity have been used with clinical effect. When used in a blood environment (e.g. for haemostasis), the patient's endogenous factor XIII will be present to effect clot cross-linking. Where this is not the case it is possible that the presence of factor XIII in the product might be beneficial. Since factor XIII is a catalytic enzyme it can operate effectively even at low concentration.

The present invention therefore further provides a method the co-purification of fibrinogen and factor XIII comprising use of immobilised metal ion affinity chromatography. Preferably, the method comprises the steps of:

(a) loading a solution comprising fibrinogen and factor XIII onto an immobilised metal ion affinity chromatography matrix under conditions such that the fibrinogen and the factor XIII both bind to the matrix, and (b) selectively co-eluting the fibrinogen and the factor XIII from the matrix.

Optionally, the fibrinogen-containing starting material may be subjected to a solvent-detergent virus inactivation treatment prior to the immobilised metal ion affinity chromatography. Solvent detergent virus inactivation may be carried out using reagents and methods known in the art (see for example U.S. Pat. No. 4,481,189, U.S. Pat. No. 4,613,501 and U.S. Pat. No. 4,540,573, all of which are hereby incorporated by reference). Suitable solvents include tri-n-butyl phosphate (TnBP) and ether, preferably TnBP. Suitable detergents include polysorbate (Tween) 80, polysorbate (Tween) 20 and Triton X-100. A preferred detergent is polysorbate 20 and a particularly preferred combination is polysorbate 20 and TnBP.

The fibrinogen-containing fraction may be stirred with solvent and detergent reagents at a temperature and for a time sufficient to inactivate any enveloped viruses that may be present. For example, the solvent detergent treatment may be carried out for about 1 hour at 25° C.

The fibrinogen recovered from the chromatography step may then be further processed in order to formulate it for pharmaceutical use. For example, it may be concentrated by ultrafiltration to a concentration of approximately 15-30 mg/ml, and/or subjected to a further pathogen reduction step, for example nanofiltration.

The concentrate may then be formulated by the addition of a combination of suitable stabilisers, for example an amino acid, a carbohydrate, a salt, and a detergent. Particularly preferably, the product is formulated without the addition of any anti-fibrinolytic agents or stabilising proteins such as albumin. The formulated product may then be sterilised by filtration and lyophilised (freeze-dried) for long term storage. Optionally, the freeze-dried product may be subjected to a dry heat treatment in a further virus inactivation step. For example, it may be heated to about 80° C. for about 72 hours or about 100° C. for about 24 hours.

The combination of the amino acid, salt, carbohydrate and detergent used to formulate the fibrinogen product assists in stabilising it across the freeze-drying and terminal heat treatment step. It also facilitates the reconstitution of the freeze-dried product. In particular, the stabilisers help stabilise any factor XIII present in the product, which is known to be highly labile.

The lyophilised and heat treated product may be reconstituted with water at ambient temperature in less than 15 minutes, preferably less than 10 minutes and most preferably less than 5 minutes to provide a solution of fibrinogen with a concentration of at least about 60 mg/ml.

It is an advantageous feature of the process of the invention that plasminogen is removed, thus avoiding the need for the addition of anti-fibrinolytic agents to the final fibrinogen preparation.

As a further feature of the invention there is therefore provided a lyophilised, preferably heat-treated, fibrinogen preparation comprising fibrinogen prepared according to one of the methods of the invention, a carbohydrate, a buffer, a salt, an amino acid and a detergent, and optionally factor XIII, the preparation being capable of dissolution in water at ambient temperature in less than 15 minutes, preferably less than 10 minutes and more preferably less than 5 minutes to give a fibrinogen solution. Preferably the concentration of fibrinogen in the final solution is at least about 60 mg/ml.

Without wishing to be bound by any theory, it is believed that combination of the salt, the detergent, the amino acid and the carbohydrate facilitate rapid dissolution of the preparation. The carbohydrate is also believed to help preserve any factor XIII activity present. The buffer controls the pH of the formulation. The use of a combination of a carbohydrate, a buffer, a salt, an amino acid and a detergent in the preparation also stabilises the fibrinogen, and any factor XIII present, without the need to add any other stabilisers, for example other proteins such as albumin. This is advantageous as addition of other proteins may be a source of viral or other contamination of the product. The fibrinogen preparations of the invention are thus free of stabilising proteins, in particular albumin. Preferably, the fibrinogen preparations of the invention are also free of anti-fibrinolytic agents.

Suitable amino acids include arginine, suitable carbohydrates include sucrose, trehalose and raffinose, preferably sucrose, suitable buffers include citrate salts (e.g. sodium citrate) and phosphate salts (e.g. sodium phosphate), suitable salts include sodium chloride and suitable detergents include polysorbate 20.

Preferably, the detergent used in the final formulation is the same detergent used for any earlier solvent detergent virus inactivation step, the amino acid formulant is the same one used to elute the fibrinogen from the metal chelate column, and the salt and buffer components are the same ones used during used during purification thereby avoiding the need to remove trace amounts of these components from the product. It is also desirable to minimise the exposure of the product to a multiplicity of reagents during manufacture, as each reagent used is a source of possible contamination or unwanted modification of the product. Thus it is preferable if the final product formulants are reagents which have already been used during processing.

Suitable concentrations of the various components will depend on the exact nature and source of the fibrinogen and may be determined using routine trial and error experiments. Suitable concentration ranges before freeze drying include:

carbohydrate (preferably sucrose): about 0.5-2.5% w/w;

detergent (preferably polysorbate 20): about 0.1-0.5% w/w;

salt (preferably sodium chloride): about 50-250 mM, preferably about 50 mM;

amino acid (preferably arginine): about 50-120 mM, preferably about 110 mM.

Sufficient buffer is added to control the pH as desired, for example at about pH 7.5.

Preferred formulations comprise about 0.5-2.5% w/w sucrose, about 0.1-0.5% w/w polysorbate 20, about 50-250 mM, more preferably about 50 mM, sodium chloride, and about 50-120 mM arginine at about pH 7.5.

The fibrinogen preparations of the invention are prepared by forming a solution of the components and then lyophilising the solution. After lyophilisation, the dry preparation is preferably subjected to a terminal heat treatment step in order to inactivate enveloped and non-enveloped viruses. For example, it may be heated to about 80° C. for about 72 hours, or to about 100° C. for about 24 hours. Heat treatment is known to be able to denature proteins, which can cause aggregation and reduce the solubility of the heat treated product.

The other ingredients in the preparations of the invention help to stabilise the fibrinogen, and any factor XIII present, during the heat treatment step.

A more detailed description of preferred embodiments of the invention is now given:

Cryoprecipitate Recovery from Plasma

Frozen human plasma may be conditioned at around −11° C., thawed to between −0.5 and 2° C. and the resulting cryoprecipitate recovered by centrifugation. The cryoprecipitate may be washed at <4° C. and recovered by centrifugation. The cryoprecipitate may be stored frozen.

Precipitation

The cryoprecipitate may be thawed with buffer (i.e. redissolved) to recover the proteins contained therein. The fibrinogen, fibronectin and factor XIII may then be precipitated using a suitable chemical agent, for example heparin, polyethylene glycol (PEG) or ethanol, or by adjustment of temperature and pH. The precipitate is then recovered, for example by centrifugation. This precipitate may be stored frozen.

Resuspension of the Precipitate

The heparin or other precipitate may then be resuspended using an appropriate buffer and mixing for a suitable time and at a suitable temperature. The resulting preparation may then be clarified, for example by depth filtration or centrifugation, prior to 0.45 μm filtration or smaller to remove any aggregates which may be present and which might shield viruses from the solvent-detergent inactivation reagents.

Solvent Detergent Treatment

Solvent and detergent may then be added to the filtrate, and the mixture stirred at a suitable temperature so as to inactivate enveloped viruses. The solvent is preferably tri-n-butyl phosphate (TnBP), whereas the detergent can be polysorbate 20, polysorbate 80 or Triton X-100, preferably polysorbate 20.

Chromatography

The solvent detergent treated material may then be applied directly to a metal chelate chromatography column, where the metal ion can be copper or any other suitable ion. Buffer conditions and loading are such that the solvent and detergent components are not retained by the adsorbent whereas fibrinogen is. Any plasminogen which is bound may then be selectively eluted using a low concentration of a low molecular weight chelating compound, for example alanine. The eluate wash fraction containing the plasminogen may then be further processed to yield a concentrate of plasminogen which may be used clinically. The fibrinogen may then be eluted at high yield using a higher concentration of the same or another chelating compound, for example arginine. Factor XIII is co-eluted with the fibrinogen. Fibrinogen is generally present in the eluate at concentrations of about 3-20 mg/ml.

The column elution may be monitored by any suitable method, for example by UV absorbance at a wavelength of 280 nanometers. This gives a measure of the protein concentration in the eluate and can be used to cue fraction collection and/or buffer changes.

Concentration

Optionally, the fibrinogen eluate may be concentrated using ultrafiltration to give final concentrations of about 15-30 mg/ml, preferably about 20-25 mg/ml.

Formulation

The fibrinogen concentrate may be formulated by the addition of a combination of an amino acid, a carbohydrate, a buffer, a salt and a detergent. The formulated product may then be sterilised by filtration to 0.2 μm and filled. Such filtration may remove or reduce viruses and other pathogens, for example the causative agent of Transmissible Spongiform Encephalopathies (TSE), currently believed to be prions. The formulation buffer (and freeze-drying conditions) are preferably chosen such that the fibrinogen plug may be reconstituted in water at room temperature in less than 10 minutes. A preferred formulation is 110 mM arginine, 1.5% w/w sucrose, 0.1% w/w polysorbate 20, 50 mM NaCl, 10 mM trisodium citrate.

Freeze-Drying and Heat Treatment

The product is freeze dried and then optionally heat treated at elevated temperatures in order to inactivate enveloped and non-enveloped viruses.

Microbiological contamination during the process is minimised by suitable sanitization of the IMAC medium and by filtration of buffers to remove bacterial contamination (e.g. by use of 0.2 μm filters).

The fibrinogen prepared using the process of the invention may be used clinically, either alone or in combination with thrombin in a fibrin sealant kit. The present invention therefore also provides fibrinogen obtained according to the process of the invention, for use in therapy, and pharmaceutical kits comprising fibrinogen obtained according the process of the invention in combination with thrombin. Preferred are kits comprising fibrinogen prepared according to the process of the invention and thrombin prepared according to the applicant's co-pending PCT application No. (unknown) entitled "Process for the preparation of thrombin" filed on 7 Jul. 2003 claiming priority from UK patent application No. 0216002.6 filed on 10 Jul. 2002, the disclosure of which is hereby incorporated by reference.

The invention will be further illustrated with reference to the following non-limiting Examples.

Fibrinogen was measured using the following methods: Heat Precipitation Assay based on a method published by Desvignes, P. and Bonnet, P., "Direct Determination of Plasma Fibrinogen levels by Heat Precipitation. A comparison of the Technique against Thrombin Clottable Fibrinogen with Spectrophotometry and Radial Immune Diffusion", Clinica Chimica Acta, 110 (1981), 9-17. Clot Time assay based on the method of Clauss (Clauss, A., Gerinnungsphysiologische Schnellmethode zur Bestimmung des Fibrinogens. Acta Haematol 1957; 17:234-46). Total Clottable Assay based on a method by Blomback and Blomback, Arkiv fur Chemi., 1956, Chapter 10, 415-443.

Factor XIII was measured by photometric determination (standard-normal human plasma). The method was based on the following references:

Fickenscher, K., Aab, A., Stuber, W., "A Photometric Assay for Blood Coagulation Factor XIII", Thromb. Haemostas. 65 (1991), 535-540 and Solleder, E., Demuth, D., Pfeiffer, C., Bomhard, M., Mayer, J., Eller, T., Brauer, P., Keller, F., Grun, J., Fickenscher, K., Wagner, C., "Klinische Prufung eines neuen photometrischen Tests zur Bestimmung der Factor XIII Aktivitat im Plasma", Lab Med. 16 (1992), 48-53.

Plasminogen and factor XIII were measured by ELISA.

Example 1

Cryoprecipitate Recovery from Plasma

Plasma was stored at less than −30° C. until use. The required weight of plasma was then conditioned at −11° C. before stripping the packaging. The plasma pool was then thawed at <2.5° C. in order to recover the fibrinogen, factor VIII, von Willebrand factor (vWF) and fibronectin cryoprecipitate from the plasma. This precipitate was recovered by centrifugation and stored frozen.

Example 2

Precipitation

Cryoprecipitate prepared according to Example 1 was resuspended in 20 mM Tris/HCl pH 6.7 to a ratio of 0.024× the net plasma pool weight and thawed by warming to between 20 and 40° C. for >20 minutes. The pH was then adjusted to 6.55 with 0.1 M HCl. A stock heparin solution was then added to give a final concentration of 0.88 mg/ml and the resulting mixture stirred for >2 minutes. This resulted in the precipitation of fibrinogen and fibronectin leaving factor VIII and vWF in solution. The heparin precipitate was then recovered by centrifugation. This precipitate may be stored frozen.

Example 3

Resuspension of the Precipitate

Heparin precipitate prepared according to Example 2 was resuspended in 20 mM $NaH_2PO_4/Na_2HPO_4$, 10 mM trisodium citrate, 0.5 M NaCl pH 6.0 in a ratio of 1 part precipitate to 5 parts buffer. This suspension was then warmed to 40° C. and incubated with mixing for >1 hour. The resuspended heparin precipitate was then clarified by filtration through two depth filters (Cuno 05SP and Cuno 30LA) and a membrane filter (Sartobran 0.65/0.45 µm) to ensure the removal of aggregates which may shield viruses from the subsequent solvent detergent treatment.

Example 4

Solvent Detergent Treatment

A solvent detergent stock solution of 20% v/v polysorbate 20 and 6% v/v TnBP was then added to the filtrate to give a final concentration of 1% v/v polysorbate 20 and 0.3% v/v TnBP. The resulting mixture was then stirred for not less than 1 hour at room temperature.

Example 5

Chromatography

The solvent detergent treated heparin precipitate prepared according to Example 4 was loaded onto a copper charged Toyopearl AF chelate 650(M) column which had been pre-equilibrated with not less than 5 bed volumes of buffer 1 (EW1: 20 mM $NaH_2PO_4/Na_2HPO_4$, 10 mM trisodium citrate, 0.5 M NaCl pH 6.0). The column was then loaded with 3 bed volumes of treated heparin precipitate. The rate of loading was no greater than 77 cm/hr. The bed was then washed with 18 bed volumes of buffer 1. The bound plasminogen was washed off using 15 bed volumes of buffer 2 (EW2: 20 mM $Na_2HPO_4$, 15 mM alanine, 0.5 M NaCl pH 7.5). The eluted plasminogen may be further processed to yield a concentrate which may be used clinically. Buffer conditions were then adjusted using bed volumes of buffer 3 (EW3: 10 mM trisodium citrate, 50 mM NaCl pH 7.0). The bound fibrinogen was then eluted using sufficient bed volumes of buffer 4 (EW4: 50 mM arginine, 10 mM trisodium citrate, 50 mM NaCl pH 7.5) such that the A280 nm (UV absorbance at a wavelength of 280 nm) returned to baseline.

The copper ions were then stripped from the resin using 5 bed volumes of 20 mM $Na_2HPO_4$, 0.25 M NaCl, 50 mM EDTA pH 7.0.

Example 6

Concentration

The eluted fibrinogen prepared according to Example 5 was concentrated using a 100 kDa molecular weight cut off membrane (Sartocon Sartorius). The membrane was pre-washed using 50 mM arginine, 10 mM trisodium citrate, 50 mM NaCl pH 7.5. The target concentration of fibrinogen was 22 mg/ml.

Example 7

Formulation

The concentrated fibrinogen solution prepared according to Example 6 was formulated by the addition of 710 mM arginine, 16.5% w/w sucrose, 1.1% w/w polysorbate 20, 50 mM NaCl, 10 mM trisodium citrate pH 7.5 at a ratio of 1:10. The final formulation concentrations were 110 mM arginine, 1.5% w/w sucrose, 0.1% w/w polysorbate 20, 50 mM NaCl, 10 mM trisodium citrate. The formulated product was then filtered to 0.2 µm (Sartobran 0.45/0.2 µm, Sartorius).

Example 8

Freeze-Drying and Heat Treatment

The product of Example 7 was aseptically filled into glass vials at 15 ml per vial and then freeze dried, stoppered and over sealed. The vials were heat treated at 80° C. for not less than 72 hours in order to inactivate non-enveloped and enveloped viruses.

Example 9

Pilot Scale Chromatography of Fibrinogen Concentrate 1274 g of heparin precipitate (prepared according to Example 2) was re-suspended in a 5 fold volume of 20 mM $NaH_2PO_4/Na_2HPO_4$, 10 mM trisodium citrate, 0.5 M NaCl pH 6.0 at 40° C. in a water bath with constant stirring for greater than 1 hour. The resultant solution was filtered to 0.45 µm with the Cuno 05SP, Cuno 30LA and Sartobran P 0.65/0.45 µm filter train. The solvent detergent mixture was then added to give final concentrations of it v/v polysorbate 20 and 0.3% v/v TnBP. The mixture was then stirred at room temperature for 1 hour.

6391 g of solvent detergent treated heparin precipitate was loaded onto 2123 mL of Toyopearl AF Chelate 650(M) resin packed into a Amicon Vantage 130 column to give a settled height of 16 cm. The chromatography column was sanitised using 5 bed volumes of 0.5 M NaOH and equilibrated with approximately 5 bed volumes of buffer 1 (EW1, 20 mM $NaH_2PO_4/Na_2HPO_4$, 10 mM trisodium citrate, 0.5 M NaCl pH 6.0). This was washed through with approximately 5 bed volumes of distilled water. The resin was then charged with metal ions using approximately 5 bed volumes of a 3 mg/ml copper sulphate solution. Loosely bound metal ions were removed using approximately 5 bed volumes of 50 mM arginine, 10 mM trisodium citrate, 50 mM NaCl pH 7.5 and then approximately 10 bed volumes of buffer 1. The load was then applied, and the bed then washed with approximately 18 bed volumes of buffer 1. The bound plasminogen was washed off using approximately 16 bed volumes of buffer 2 (EW2: 20 mM NaH$_2$PO$_4$/Na$_2$HPO$_4$, 15 mM alanine, 0.5 M NaCl pH 7.5). Buffer conditions were then adjusted using approximately 5 bed volumes of buffer 3 (EW3: 10 mM trisodium citrate, 50 mM NaCl pH 7.0). The bound fibrinogen was then eluted using approximately 5 bed volumes of buffer 4 (EW4: 50 mM arginine, 10 mM trisodium citrate, 50 mM NaCl pH 7.5). The copper ions were then stripped from the resin using approximately 5 bed volumes of 20 mM Na$_2$HPO$_4$, 0.25 M NaCl, 50 mM EDTA pH 7.0.

The concentrations and recovery data for fibrinogen, plasminogen and Factor XIII are given in Table 1. The clearance of TnBP and polysorbate 20 are given in Table 2.

TABLE 1

| Sample | Volume ml | Fibrinogen mg/ml | Fibrinogen % | Factor XIII U/ml | Factor XIII % | Plasminogen µg/ml | Plasminogen % |
|---|---|---|---|---|---|---|---|
| Load | 6391 | 11.81 | (100) | 0.8 | (100) | 43.9 | (100) |
| FT | 6407 | <1 | <8.49 | | | 0.01 | 0.02 |
| EW1 | 31971 | <1 | <42.36 | 0.01 | 6.25 | 0.03 | 0.34 |
| EW2 | 33800 | <1 | <44.78 | 0.05 | 33.06 | 7.74 | 93.25 |
| EW3 | 10674 | <1 | <14.14 | 0.05 | 10.44 | 0.20 | 0.76 |
| EP1 | 680 | | | | | | |
| EP2 | 8943 | 6.45 | 76.43 | 0.32 | 55.98 | 4.00 | 12.75 |
| EP3 | 2060 | | | | | | |
| EDTA | 9155 | <1 | <12.13 | | | 0.01 | 0.03 |

Abbreviations used: FT = flowthrough; EW1 = equilibration wash 1; EW2 = equilibration wash 2; EW3 = equilibration wash 3; EP1 = elution peak 1 (leading edge of elution peak); EP2 = elution peak 2 (main elution peak); EP3 = elution peak 3 (trailing edge of the elution peak).

TABLE 2

| | | TnBP | | Polysorbate 20 | |
|---|---|---|---|---|---|
| Sample | Volume (ml) | Conc. (mg/l) | Recovery (%) | Conc. (mg/l) | Recovery (%) |
| Load | 6391 | 2900 | (100) | 13700 | (100) |
| EP2 | 8943 | 6.9 | 0.3 | 38 | 0.4 |

Abbreviations used: EP2 = elution peak 2 (main elution peak).

The results showed that the three proteins, fibrinogen, plasminogen and factor XIII, were efficiently captured on the Cu$^{2+}$ loaded Toyopearl and then 93% of the loaded plasminogen was selectively removed by washing with the 15 mM alanine buffer (EW2). The eluted fibrinogen product contained 76% and 56% of the applied fibrinogen and factor XIII respectively. The clearance of solvent detergent chemicals was also efficient: only 0.3 and 0.4% of the applied TnBP and polysorbate 20, respectively, were left in the product after chromatography.

Example 10

Pilot Scale Ultrafiltration of Fibrinogen

Two polysulphone Sartorius slice cassettes (0.1 m$^2$ each) were assembled into a Sartorius membrane holder and flushed with 7 l deionised water. The assembly was sanitised with a 1 l flush of 1 M NaOH warmed to 40° C. and then 5 l of NaOH, recirculated for 1 hour. The system was then flushed with 10 l deionised water at a cross flow velocity of 880 ml/min. The membrane was prepared with 5 l of EW4 (50 mM arginine, 10 mM trisodium citrate, 50 mM NaCl pH 7.5) with no applied back-pressure at the same cross-flow velocity.

8960 ml of eluted fibrinogen fraction was applied at an initial fibrinogen concentration of 5.24 mg/ml at a maximum inlet pressure and trans-membrane pressure of 1.4 and 0.7 bar (140,000 and 70,000 Pa) respectively. The ultrafiltration took 1 hour 36 minutes and gave a retentate of 1227 ml and 23.8 mg/ml fibrinogen. The average flux was 28.8 L/m$^2$/h and predicted gelling concentrations was 31.0 mg/ml.

Example 11

Choice of IMAC Gels for Purification of Fibrinogen

Several metal chelate chromatography gels were tested for their ability to bind and subsequently release fibrinogen. These are described in Table 3 below:

TABLE 3

| Gel | Manufacturer | Base Matrix | Chelating group |
|---|---|---|---|
| Toyopearl Chelate AF | Tosoh Biosep | Methacrylate | iminodiacetic acid |
| Toyopearl Chelate AF (modified spacer arm) | Tosoh Biosep | Methacrylate | iminodiacetic acid |
| Fractogel EMD Chelate | Merck | Methacrylate | iminodiacetic acid |
| Chelating Sepharose FF | Amersham Biosciences | Cross-linked agarose | iminodiacetic acid |

The starting material was cryoprecipitate which contained fibrinogen. This precipitate was redissolved in Buffer I (20 mM sodium phosphate buffer containing either 250 mM sodium chloride or 500 mM sodium chloride, pH 7). The chelating gel was charged with metal ions (copper, nickel or zinc) then equilibrated with Buffer I. The redissolved cryoprecipitate was applied to a packed column containing the charged, equilibrated gel. After all the material had been applied, the column was washed with Buffer I. The fibrinogen was eluted by washing the column with Buffer II (20 mM sodium phosphate, 0.05 M EDTA buffer containing either 250 mM sodium chloride or 500 mM sodium chloride, pH 7) or Buffer III (20 mM sodium phosphate, 50 mM arginine, 250 mM sodium chloride, pH 7.5) or Buffer IV (20 mM sodium phosphate, 200 mM arginine, 250 mM sodium chloride pH 7.0).

The results are shown in Table 4.

TABLE 4

| Gel | Metal ion | Fibrinogen eluted, mg per ml of gel | Factor XIII eluted, u/mg fibrinogen |
|---|---|---|---|
| Toyopearl Chelate AF (Tosoh Biosep) | copper | 38.7[a] | 0.3 |
| Toyopearl Chelate AF (Tosoh Biosep) | copper | 24.1[b] | 0.1 |
| Toyopearl Chelate AF (modified spacer arm) (Tosoh Biosep) | copper | 35.6[b] | 0.08 |
| Fractogel EMD Chelate (Merck) | copper | 30.8[a] | 0.26 |
| Chelating Sepharose FF | copper | 16.1[a] | not tested |

TABLE 4-continued

| Gel | Metal ion | Fibrinogen eluted, mg per ml of gel | Factor XIII eluted, u/mg fibrinogen |
|---|---|---|---|
| (Amersham Biosciences) | | | |
| Toyopearl Chelate AF (Tosoh Biosep) | zinc | 23.5[a] | 0.22 |
| Fractogel EMD Chelate (Merck) | zinc | 31[a] | 0.27 |
| Chelating Sepharose FF (Amersham Biosciences) | zinc | 11.5[a] | not tested |
| Toyopearl Chelate AF (Tosoh Biosep) | nickel | 23.7[c] | not tested |

[a]Eluted with Buffer II.
[b]Eluted with Buffer III.
[c]Eluted with Buffer IV.

The results show that fibrinogen and factor XIII can be isolated from a fibrinogen-containing solution using immobilised metal ion affinity chromatography (IMAC) with a variety of IMAC base matrix chemistries and metal ions.

Example 12

Choice of Starting Materials

The ability of immobilised metal ion affinity chromatography (IMAC) to purify fibrinogen from different fibrinogen-containing solutions was investigated.

Fibrinogen-Containing Solutions:
  A. Redissolved Cryoprecipitate obtained from thawed human plasma (prepared according to Example 1).
  B. Redissolved Heparin Precipitate obtained from redissolved cryoprecipitate which had been mixed with heparin (prepared according to Example 2).
  C. Redissolved Cold Precipitate obtained by chilling redissolved cryoprecipitate.
  D. Fibrinogen-containing solution chromatographically depleted of factor VIII, von Willebrand factor (vWF) and fibronectin, obtained from human plasma.

The cold precipitate used in C was prepared as follows: cryoprecipitate, prepared as in Example 1, was redissolved in four times its weight of 50 μM calcium chloride solution at 28° C. pH was adjusted to 6.8 with 1 M acetic acid and the solution cooled to 10° C. After mixing for >10 minutes, the precipitate which formed was collected by centrifugation.

Each solution A-D, containing approximately 1-20 mg fibrinogen per ml, was incubated with solvent and detergent to inactivate viruses, then applied to a column of Toyopearl Chelate IMAC resin which had been charged with copper ions and equilibrated with 20 mM sodium phosphate, 250 mM sodium chloride pH 7.0. After loading, the resin was washed with the same buffer. Fibrinogen was eluted by application of 25 mM imidazole (Buffer X) or 50 mM arginine 20 mM sodium phosphate, 250 mM sodium chloride pH 7.5 (Buffer Y).

The results are shown in Table 5.

TABLE 5

| Start Material | Fibrinogen in Start Material, mg/ml | Elution Buffer | Fibrinogen in eluate, mg per ml of resin |
|---|---|---|---|
| A: cryo-precipitate | 14.1 | X | 29.8 |
| C: cold precipitate | 21.6 | X | 29.0 |
| D: fibrinogen solution | 0.73 | X | 38.7 |
| A: cryo-precipitate | 11.1 | Y | 32.5 |
| B: heparin precipitate | 14.8 | Y | 29.9 |
| C: cold precipitate | 20.9 | Y | 31.4 |

The results show that IMAC can be used to prepare fibrinogen from different fibrinogen-containing starting materials.

Example 13

Formulation of Fibrinogen to Allow Rapid Re-Solution After Freeze-Drying and Heat-Treatment Fibrinogen which had been eluted from IMAC resin according to Examples 9 and 10 and concentrated to approximately 15 mg/ml in 50 mM Arginine, 20 mM phosphate pH 7.5 (Tables 6 and 8) or 50 mM Arginine, 10 mM tri-sodium citrate pH 7.5 (Table 7) was formulated with various added compounds, filled into glass vials (20 ml per vial) and freeze-dried. On completion of freeze-drying, the vials were sealed under vacuum, then heat-treated at 80° C. for 72 hours to inactivate viruses. The vials were then reconstituted with water (5 ml per vial) at ambient room temperature (18° C.-25° C.). Re-solution time was measured, as the time between addition of water and the time at which a clear homogeneous solution without residual solid matter was observed.

The results are shown in Tables 6, 7 and 8.

TABLE 6

| Arg mM | Polys % | NaCl mM | Cit mM | Suc % | Recons time, mins | Fib after recons, mg/ml | Factor XIII after recons, u/ml |
|---|---|---|---|---|---|---|---|
| 50 | 0.5 | 250 | 10 | 1.5 | 4.5 | 44.3 | <1 |
| 50 | 0.1 | 250 | 10 | 1.5 | 8.1 | 49.3 | <1 |
| 50 | 0.5 | 250 | 0 | 0 | 4.1 | 40.0 | <0.5 |
| 50 | 0.5 | 250 | 10 | 1.5 | 6.5 | 37.0 | <0.5 |
| 50 | 0.5 | 250 | 0 | 1.5 | 5.8 | 33.1 | <0.5 |
| 50 | 0.25 | 250 | 0 | 1.5 | 4.9 | 35.4 | <0.5 |
| 50 | 0.1 | 250 | 0 | 1.5 | 3.9 | 39.9 | <0.5 |
| 50 | 0.5 | 230 | 0 | 1.5 | 4.5 | 36.6 | <0.5 |
| 50 | 0.5 | 200 | 0 | 1.5 | 3.6 | 37.5 | <0.5 |
| 50 | 0.5 | 180 | 0 | 1.5 | 4.9 | 35.0 | <0.5 |
| 50 | 0.5 | 150 | 0 | 1.5 | 4.2 | 37.9 | <0.5 |
| 50 | 0.5 | 130 | 0 | 1.5 | 5.7 | 36.8 | <0.5 |
| 50 | 0.5 | 100 | 0 | 1.5 | 7.1 | 36.9 | <0.5 |
| 50 | 0.5 | 80 | 0 | 1.5 | 7.8 | 36.9 | <0.5 |
| 50 | 0.5 | 50 | 0 | 1.5 | 12.2 | 41.3 | 1.2 |
| 50 | 0.5 | 50 | 10 | 1.5 | 8.6 | 43.3 | 1.3 |
| 50 | 0.5 | 50 | 0 | 2.5 | 7.6 | 40.7 | 1.2 |

TABLE 7

| Arg mM | Polys % | NaCl mM | Phos mM | Suc % | Recons time, mins | Fib. after recons, mg/ml | Factor XIII after recons, u/ml |
|---|---|---|---|---|---|---|---|
| 50 | 0.5 | 250 | | | 6.3 | 63.7 | <1.5 |
| 50 | 0.5 | 50 | | 1.5 | 4.5 | 67 | 2.4 |
| 50 | 0.5 | 50 | 20 | 1.5 | 2.1 | 63 | 1.9 |
| 50 | 0.25 | 50 | | 1.5 | 1.4 | 71.7 | 1.8 |
| 50 | 0.1 | 50 | | 1.5 | 1.6 | 61.9 | 1.8 |
| 50 | 0.25 | 50 | 20 | 1.5 | 2.0 | 62.1 | 1.8 |
| 50 | 0.1 | 50 | 20 | 1.5 | 2.6 | 70.8 | 1.7 |
| 50 | 0.5 | 50 | | 1 | 4.3 | 70.1 | 2.0 |
| 50 | 0.5 | 50 | | 0.75 | 2.7 | 69.1 | 2.0 |
| 50 | 0.5 | 50 | | 0.5 | 2.6 | 73.3 | 1.7 |
| 50 | 0.25 | 50 | | 0.75 | 3.0 | 71.7 | 1.8 |
| 100 | 0.1 | 50 | | 1.5 | 8.8 | 54.8 | 1.3 |
| 50 | 0.1 | 250 | | | 7.2 | 53.7 | <1 |
| 120 | 0.1 | 50 | | 1.5 | 5.7 | 55.4 | <1 |

TABLE 8

| Arg mM | Poly % | NaCl mM | Cit mM | Carbo % | Recons time, mins | Fib after recons, mg/ml | Factor XIII after recons, u/ml |
|---|---|---|---|---|---|---|---|
| 50 | 0.5 | 50 | 0 | sucrose 1.5% | 12.2 | 41.3 | 1.2 |
| 50 | 0.5 | 50 | 0 | trehalose 1.5% | 14.5 | 41.1 | 1.2 |
| 50 | 0.5 | 50 | 0 | raffinose 1.5% | 13.9 | 42.5 | 1.3 |

Abbreviations used in Tables 6-8:
Arg = arginine
Poly = polysorbate 20
Cit = citrate
Suc = sucrose
Fib = fibrinogen
Recons = reconstitution
Carbo = carbohydrate
Phos = phosphate The results showed that effective concentration ranges of the formulants were:
Sucrose: 0.5-2.5%
Polysorbate 20: 0.1-0.5%
Sodium Chloride: 50-250 mM (50 mM for factor XIII retention)
Arginine: 50-120 mM High concentrations of sodium chloride (250 mM) in combination with arginine, polysorbate 20 and a buffer salt allowed rapid re-constitution of freeze-dried, heat-treated fibrinogen but factor XIII activity was lost. Reduction in the sodium chloride content accompanied by the addition of sucrose allowed both rapid reconstitution and the retention of factor XIII activity.

Selective combinations of arginine, polysorbate 20, sodium chloride, a suitable buffering salt and a carbohydrate provided a formulation for fibrinogen and factor XIII which enabled rapid reconstitution of freeze-dried, heat-treated product at room temperature, with retention of fibrinogen and factor XIII activity.

Example 14

Ultrafiltration, Formulation, Freeze Drying and Heat Treatment

In four independent experiments (A-D), a heparin precipitate was resuspended according to Example 3 and solvent detergent treated according to Example 4. The resulting solution was separated by chromatography according to Example 9 to give an eluate rich in fibrinogen and factor XIII. This eluate was then concentrated according to Example 10. The concentrate was formulated to a target of 110 mM arginine, 1.5% w/w sucrose, 0.1% w/w polysorbate 20, 50 mM NaCl, 10 mM trisodium citrate and sterile filtered to 0.2 µm according to Example 7. The filtered concentrate was then aseptically filled, freeze-dried and heat-treated according to Example 8 to give a double viral inactivated product.

The eluates, filtered concentrates and products were assayed for clottable protein and factor XIII activity, and the results are shown in Table 9.

TABLE 9

| Fraction | property | A | B | C | D |
|---|---|---|---|---|---|
| eluate | Clottable protein (mg/mL) | 5.8 | 5.6 | 4.4 | 4.52 |
| | factor XIII activity (U/mL) | 0.19 | 0.41 | 0.18 | 0.18 |
| filtered concentrate | Clottable protein (mg/mL) | 21.2 | 20.4 | 22.1 | 18.2 |
| | factor XIII activity (U/mL) | 0.61 | 1.43 | 0.68 | 0.65 |
| product | Clottable protein (mg/mL) | 63.3 | 45.9 | 48.8 | 46.3 |
| | factor XIII activity (U/mL) | 1.19 | 1.64 | 1.25 | 1.17 |
| | reconstitution time (min) | 9.05 | 5.35 | 8.72 | 11.22 |

The results show that the fibrinogen can be concentrated to approximately 20 mg/mL using ultrafiltration. They also show that the formulation conditions give a product with a concentration of factor XIII of >1 U/mL and reconstitution times <<15 min.

Example 15

The Effect of Elution Buffer Concentration and pH on Elution of Fibrinogen and Copper from a Chelate Resin Cryoprecipitate was redissolved in buffer 1 (20 mM phosphate buffer containing 0.25 M NaCl pH 6.0) and solvent detergent treated as Example 4. Chelate resin (Toyopearl AF Chelate 650 (M)) was charged with copper ions, pre-washed with the appropriate elution buffer and then equilibrated with buffer 1. This material was loaded onto the packed, copper charged resin. After all the material had been applied, the column was washed with fifteen to twenty volumes of buffer 1. The column was then washed with five to seven bed volumes of buffer 2 (20 mM phosphate buffer containing 0.25 M NaCl pH 7.0). The column was eluted with a buffer containing 20 mM phosphate, 0.25 M NaCl and arginine at a range of concentrations and pH.

The results are shown in Table 10.

TABLE 10

| Arginine Concentration in elution buffer | elution Buffer pH | Concentration of Eluted Fibrinogen mg/ml | mgs of Fibrinogen Eluted/ml of Resin | Concentration of Eluted Copper mg/L | μg Copper/mg of Eluted fibrinogen |
|---|---|---|---|---|---|
| 200 | 7 | 4.5 | 32.3 | 8 | 1.8 |
| 100 | 7 | 4.8 | 35.7 | 4.6 | 0.95 |
| 50 | 7 | 2.5 | 17.5 | 2 | 0.8 |
| 50 | 6.0 | 1.9 | 17.6 | 1.4 | 0.74 |
| 50 | 7.5 | 4.4 | 33.3 | 2 | 0.46 |
| 50 | 8.0 | 3.96 | 35.3 | 2.5 | 0.63 |

The results showed that a reduction in the concentration of arginine in the elution buffer reduced the concentration of copper in the fibrinogen eluate but had an adverse effect on the recovery of fibrinogen. An increase in the pH of the 50 mM arginine elution buffer to 7.5 resulted in high recovery of fibrinogen and the levels of copper co-eluted were substantially reduced.

Example 16

Treatment of Heparin Precipitate

Frozen heparin precipitate was re-dissolved in 20 mM sodium phosphate, 500 mM sodium chloride, 10 mM tri-sodium citrate pH 6.0 at a ratio of 1:5 by weight. Two re-solution methods were compared:

Method 1. Heparin precipitate was added to the buffer at ambient temperature. The mixture was then warmed to 40° C. and incubated at 40° C. for 1 hour.

Method 2. The buffer was pre-warmed to 40° C. and the heparin precipitate was then added at a rate which maintained a temperature of >36° C. Following addition of all precipitate, the mixture was then incubated for 1 hr at 40° C.

Three different batches of precipitate were tested. In each case, re-solution Method 2 resulted in a significantly higher filter capacity. The final filtrate weight and fibrinogen concentration was also consistently higher resulting in improved fibrinogen yields (see Table 11).

TABLE 11

| Batch | resolution method | scale of filtration[1] | Cuno 05SP filter capacity[2] (kgm$^{-2}$) | Cuno 30LA filter capacity[2] (kgm$^{-2}$) | Sartobran 0.65/0.45 mm filter capacity[2] (kgm$^{-2}$) | Fibrinogen yield[3] (%) |
|---|---|---|---|---|---|---|
| A | 1 | Bench | 10.66 | 4.57 | 3.57 | 64 |
| A | 2 | Bench | 26.31 | 26.10 | 17.51 | Not assayed |
| A | 2 | Pilot | >23.57 | >23.72 | >13.96 | 82 |
| B | 1 | Bench | 4.33 | 4.57 | 3.47 | 29 |
| B | 2 | Bench | 13.40 | 13.16 | 11.69 | Not assayed |
| C | 1 | Bench | 9.63 | 8.73 | 8.48 | 58 |
| C | 2 | Pilot | >21.66 | >22.92 | >13.96 | 81 |

Notes:
[1]Bench scale filter area = 0.00173 m$^2$; pilot scale filter area = 0.3 m$^2$. The initial applied air pressure during filtration was 0.25 bar (25,000 Pa) at bench scale and 0.1-0.2 bar (10,000-20,000 Pa) at pilot scale.
[2]Filter capacity is calculated as the maximum amount of re-solubilised material filtered divided by the filter area. Examples showing capacities "greater than" did not block the filter under experimental conditions
[3]The fibrinogen yield is calculated in this case as the mg of fibrinogen recovered from the filter (=concentration recovered mgmL$^{-1}$ × mL filtrate collected) divided by the mg fibrinogen that was in this volume of starting material (=concentration applied mgmL$^{-1}$ × mL filtrate collected) × 100(%).

What is claimed is:

1. A method for the separation and purification of fibrinogen and plasminogen which comprises the steps of:
   (a) loading a solution comprising fibrinogen and plasminogen onto an immobilized metal ion affinity chromatography matrix under conditions such that the fibrinogen and the plasminogen both bind to the matrix, and
   (b) selectively eluting the fibrinogen and the plasminogen separately from the matrix,
   wherein the immobilized metal ion affinity chromatography matrix is a copper, nickel or zinc ion affinity chromatography matrix;
   wherein plasminogen is eluted using a buffer comprising less than or equal to 20 mM of a competitive chelating compound;
   wherein fibrinogen is eluted using a buffer comprising greater than 20 mM of the same or a different competitive chelating compound; and
   wherein the competitive chelating compound is selected from the group consisting of an amino acid, imidazole, EDTA and a citrate salt.

2. A method for the separation of fibrinogen from plasminogen comprising the steps of:
   (a) loading a solution comprising fibrinogen and plasminogen onto an immobilized metal ion affinity chromatography matrix under conditions such that at least the fibrinogen binds to the matrix, and
   (b) selectively eluting the fibrinogen from the matrix,
   wherein the immobilized metal ion affinity chromatography matrix is a copper, nickel or zinc ion affinity chromatography matrix;
   wherein the fibrinogen is eluted using a buffer comprising more than 20 mM of a competitive chelating compound;
   wherein the competitive chelating compound is selected from the group consisting of an amino acid, imidazole, EDTA and a citrate salt.

3. The method according to claim 2, wherein the plasminogen and the fibrinogen are selectively eluted separately from the matrix,
   wherein plasminogen is eluted using a buffer comprising ≦20 mM of a competitive chelating compound;
   wherein the competitive chelating compound is selected from the group consisting of an amino acid, imidazole, EDTA and a citrate salt.

4. The method according to claim 1 or 2, wherein the solution comprising fibrinogen is a fibrinogen-containing plasma fraction.

5. The method of claim 1 or 2 further comprising the step of concentrating the fibrinogen by ultrafiltration to a concentration of approximately 15 to 30 mg/ml.

6. The method of claim 5 further comprising the steps of:
   combining the fibrinogen with a combination of suitable stabilizers to form a fibrinogen formulation;

sterilizing the fibrinogen formulation by filtration; and
lyophilizing the fibrinogen formulation to form a lyophilized fibrinogen formulation.

7. The method of claim 6, wherein the stabilizers are selected from the group consisting of an amino acid, a carbohydrate, a salt, and a detergent.

8. The method of claim 6 further comprising the step of subjecting the lyophilized fibrinogen formulation to dry heat treatment.

9. The method of claim 1 or 2, wherein the competitive chelating compound used to elute plasminogen is an amino acid selected from the group consisting of alanine, leucine and lysine, and the competitive chelating compound used to elute fibrinogen is an amino acid selected from the group consisting of lysine and arginine.

10. The method of claim 9, wherein the competitive chelating compound used to elute plasminogen is selected from the group consisting of $\leqq 20$ mM alanine, $\leqq 20$ mM leucine and $\leqq 10$ mM lysine.

11. The method of claim 1, wherein fibrinogen is eluted using a buffer comprising more than 20 mM of lysine, arginine or imidazole.

12. The method of claim 1 or 2, wherein the buffers for eluting plasminogen comprise a salt of, phosphate and chloride.

13. The method of claim 1 or 2, wherein the buffer for eluting plasminogen comprises 20 mM phosphate, 15 mM alanine and 0.5 M chloride and the buffer for eluting fibrinogen comprises 10 mM citrate, 50 mM arginine and 50 mM chloride.

14. The method of claim 1 or claim 2, wherein the buffers for eluting fibrinogen comprise a salt of citrate and chloride.

* * * * *